United States Patent [19]

Gutierrez et al.

[11] Patent Number: 4,486,326

[45] Date of Patent: Dec. 4, 1984

[54] COPPER COMPLEXES OF OXAZOLINES AND LACTONE OXAZOLINES AS LUBRICATING OIL ADDITIVES

[75] Inventors: Antonio Gutierrez, Mercerville; Darrell W. Brownawell, Scotch Plains; Stanley J. Brois, Westfield, all of N.J.

[73] Assignee: Exxon Research & Engineering Co., Florham Park, N.J.

[21] Appl. No.: 529,391

[22] Filed: Sep. 6, 1983

[51] Int. Cl.$^3$ .............................................. C10M 1/54
[52] U.S. Cl. .............................. 252/49.7; 252/51.5 A; 252/51.5 R; 548/101; 548/239
[58] Field of Search ............ 252/49.7, 51.5 A, 51.5 R; 548/101, 239

[56] References Cited

U.S. PATENT DOCUMENTS

| | | | |
|---|---|---|---|
| 2,587,955 | 3/1952 | Barnum | 252/34 |
| 4,035,309 | 7/1977 | Brois | 252/49.7 |
| 4,062,786 | 12/1977 | Brois et al. | 252/51.5 R |
| 4,116,876 | 9/1978 | Brois et al. | 252/49.6 |
| 4,169,836 | 10/1979 | Ryer et al. | 548/238 |
| 4,176,073 | 11/1979 | Ryer et al. | 252/49.7 |
| 4,176,074 | 11/1979 | Coupland et al. | 252/32.7 |
| 4,253,978 | 3/1981 | Gemmill, Jr. et al. | 252/49.7 |

Primary Examiner—Jacqueline V. Howard
Attorney, Agent, or Firm—J. J. Mahon

[57] ABSTRACT

There are disclosed lubricating oil compositions containing an oil soluble hydrocarbon substituted monooxazoline, bis-oxazoline or lactone oxazoline dispersant containing 0.2 to 2.0 wt % of complexed copper, the dispersant exhibiting improved varnish inhibition properties as well as providing anti-oxidation properties to the lubricating oil.

7 Claims, No Drawings

COPPER COMPLEXES OF OXAZOLINES AND LACTONE OXAZOLINES AS LUBRICATING OIL ADDITIVES

This invention relates to copper complexes of oxazoline or lactone oxazoline lubricating oil dispersants which offer improved performance as varnish inhibiting additives for lubricating oil compositions.

Oxazolines and lactone oxazoline lubricating oil additives are known in the art and are disclosed for example in U.S. Pat. Nos. 4,116,876; 4,169,836 and 4,062,786.

The use of a metal salt promoter in preparing oxazoline compounds is disclosed in U.S. Pat. No. 4,035,309 issued to Brois. the metals useful therein being zinc, cobalt, manganese, nickel and iron. Borated derivatives of oxazolines and lactone oxazolines useful as sludge dispersants in lubricating oils are disclosed in U.S. Pat. No. 4,116,876, and molybdenum complexes of oxazoline dispersants useful as friction reducing antiwear additives are disclosed in U.S. Pat. No. 4,177,074.

The use of oil soluble organic copper compounds in lubricating oil compositions is a relatively recent development of oil additive technology and the disclosure of these compounds as highly effective antioxidants is found in European publication No. 80302627.7 published on Feb. 25, 1981, which discloses the use of 5 to 500 ppm copper in the form of an oil soluble organic compound such as a copper salt of a $C_{10}$–$C_{22}$ fatty acid.

The present invention is based upon the discovery that copper may be successfully incorporated into mono-oxazoline, bis-oxazoline or lactone oxazoline dispersants to yield products exhibiting greatly improved varnish inhibition properties when formulated into lubricating oil compositions.

In accordance with the present invention there have been discovered lubricating oil compositions comprising a major amount of lubricating oil and a minor but varnish and oxidation inhibiting amount of an oil-soluble copper complex of an oil-soluble hydrocarbon substituted mono- or bis-oxazoline or a hydrocarbon substituted lactone oxazoline dispersant, the copper being present in said dispersant in an amount of about 0.2 wt% to 2 wt% of the dispersant.

The copper-containing oxazoline and lactone oxazoline dispersants of the present invention provide a number of significant advantages to lubricating oil compositions. The oils, due to the presence of the copper, will exhibit the desirable anti-oxidant properties as disclosed in said European Application No. 8030.2627.7 and also exhibit improved dispersancy as indicated by the substantial improvements in the inhibition of varnish deposits when compared with the same oxazoline and lactone oxazoline dispersants prior to being complexed with copper.

A further advantage resides in improved storage stability of lubricating oil compositions in that the copper complexed dispersants of this invention exhibit improved compatibility with other metal-containing additives customarily used in lubricating oil composition, especially the metal and overbased metal oil soluble sulfonate, phenate and sulfurized phenate detergent additives. This improved compatibility is evidenced by viscosity stability when the copper-complexed oxazoline and lactone oxazoline dispersants of this invention are blended in lubricating oil compositions with the metal detergent additives.

Dispersants are normally provided in the form of a 50% by weight concentrated solution in mineral oil of lubricating viscosity and said dispersant concentrates are incorporated into a finished lubricating oil in amounts of from about 0.5 to 7 wt% of solution concentrate based on the total weight of the lubricating oil compositions. In the compositions of the present invention it is preferred that the finished lubricating oil composition contain about 50 to 300 ppm (parts per million) of copper in the form of the copper complexed oxazoline or lactone oxazoline dispersant to provide the optimum performance in terms of both oxidation inhibition and inhibition of varnish deposits forming on engine parts.

The mono-oxazoline, bix-oxazoline and lactone oxazoline dispersants that may be complexed with certain copper compounds in accordance with the present invention are described hereinbelow and are the same materials referred to in the patents listed above.

Mono- and bis-oxazoline dispersants are prepared by reaction of a $C_4$–$C_8$ amino alcohol of the formula $NH_2—C(X)_2—CH_2OH$ wherein X is alkyl or hydroxyalkyl, at least one X being the hydroxyalkyl of the formula $—(CH_2)_mOH$, m being 1 to 3, with an oil-soluble hydrocarbon substituted $C_4$–$C_{10}$ dicarboxylic acid material (acid, anhydride, or ester), the hydrocarbon substituent having an average, based upon the Mn, of at least about 50 carbon atoms and preferably being a polymeric alkenyl group derived from a $C_2$–$C_5$ mono-olefin, e.g., ethylene, propylene, butylene, isobutylene, and pentene with polyisobutenyl being preferred herein. Examples of suitable amino-alkanols are 2-amino-2-methyl-1,3 propanediol, tris-(hydroxymethyl) aminomethane, a preferred amino-alcohol, also referred to as THAM, 2-amino-2-ethyl,1-3 propanediol and similar disubstituted amino alcohols capable of forming oxazoline ring in reaction with the oil-soluble hydrocarbon substituted dicarboxylic acid material.

The mono-oxazoline is formed by reaction of equivalent proportions of amino-alkanol and dicarboxylic acid material. The bis-oxazoline is formed by reaction of 2 moles of aminoalkanol per mole of dicarboxylic acid material at about 140°–240° C. for about 0.5 to 24 hours with or without an inert diluent.

Preferred dicarboxylic acid materials are polymers of $C_3$–$C_4$ olefins, such as polyisobutenyl succinic anhydrides wherein the polyolefinic or polyisobutenyl group has an Mn of 900 to 5,600 and especially polyisobutenyl of Mn=900–2,000.

Other suitable but less preferred dicarboxylic acid materials are those derived from $C_4$–$C_{10}$ dicarboxylic acid materials such as, fumaric acid, itaconic acid, chloromaleic acid, dimethyl fumarate and the like.

An oxazoline product is considered represented by the following structure showing a bis oxazoline:

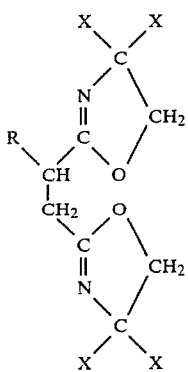

wherein R is hydrocarbyl group, such as a polyisobutenyl group, and X would be, for example, a —CH$_2$OH if THAM were the aminoalkanol used. Lactone oxazoline co-dispersants useful in the present invention are described in the U.S. Pat. No. 4,062,786 issued Dec. 13, 1977 to Brois et al. and are the reaction products of hydrocarbyl substituted lactone carboxylic acids which the above described 2,2-disubstituted-2-amino-1-alkanols.

The preferred lactone oxazoline co-dispersant is the reaction product of polyisobutenyl lactone carboxylic acid with tris-(hydroxymethyl) amino-methane at a temperature of from about 100°–240° C., preferably 150°–180° C., until two moles of H$_2$O per mole of reactant is removed from the reaction.

Generally, the lactone oxazoline co-dispersant is formed by lactonization, an intramolecular cyclization, in the presence of an acid catalyst, such as a mineral acid, a Lewis acid, or an alkanesulfonic acid, of a hydrocarbyl substituted dicarboxylic acid material (acid, anhydride, or ester), such as an alkenyl succinic acid analog obtained via the Ene reaction of an olefin with an alpha-beta unsaturated C$_4$–C$_{10}$ dicarboxylic acid, anhydride or ester such as fumaric acid, itaconic acid, maleic acid, maleic anhydride, dimethyl fumarate, and the like. The olefin source for the hydrocarbyl substituted comprises the same materials described hereinabove for the mono- and bis-oxazoline co-dispersants used in the present invention, i.e., C$_2$–C$_5$ monoolefin polymers, especially polyisobutenyl polymers.

The lactone oxazoline co-dispersant is formed by heating together the hydrocarbon substituted lactone dicarboxylic acid material noted above with the 2,2-disubstituted-2-amino-1-alkanol, preferably THAM, in at least equivalent amounts.

An example of a lactone oxazoline co-dispersant produced thereby is considered to have the following structure where the dicarboxylic acid material is a lactonized polyisobutenyl succinic anhydride and THAM is the aminoalkanol used, R represents the polyisobutenyl moiety:

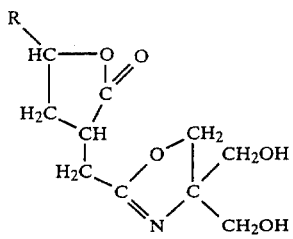

The foregoing mono-oxazolines, bis-oxazolines or lactone oxazolines are reacted with a complex-forming copper compound. Copper carboxylates of C$_1$–C$_5$ carboxylic acids, copper oxides, and thiocyanates of copper have been found especially useful in preparing the compositions of this invention.

The copper complexes of the present invention are formed by reacting the copper salts with the oxazoline or lactone oxazoline dispersant utilizing a molar ratio of about 1 mole of oxazoline or lactone oxazoline per mole of copper at elevated temperatures of about 50° C.–200° C. for about 2 to 10 hours in an inert hydrocarbon solvent such as mineral oil of lubricating viscosity, kerosene, neutral mineral oils, xylene, halogenated hydrocarbons, such as carbon tetrachloride and dichlorobenzene. Mineral oil is preferred as a reaction solvent to facilitate the use of the products as lubricating oil and additives.

It is believed that the final product is a coordination complex wherein the nitrogen contained in the oxazoline moiety is the ligand which complexes with copper.

Lubricating oil compositions of this invention will typically contain a number of conventional additives in amounts as required to provide their normal attendant functions and these include the metal detergent additives, viscosity index improvers, other anti-oxidant products, anti-wear additives and the like.

The metal detergent additives suitable in the oil formulations of the present invention are known in the art and include one or more members selected from the group consisting of overbased oil-soluble calcium, magnesium and barium phenates, sulfurized phenates, and sulfonates especially the sulfonates of C$_{16}$–C$_{50}$ alkyl substituted benzene or toluene sulfonic acids which have a total base number of about 80 to 300. These overbased materials may be used as the sole metal detergent additive or in combination with the same additives in the neutral form but the overall metal detergent additive combination should have a basicity as represented by the foregoing total base number. Preferably they are present in amounts of from about 3 to 6 wt% with a mixture of overbased magnesium sulfurized phenate and neutral calcium sulfurized phenate, obtained from C$_9$ or C$_{12}$ alkyl phenols being especially useful.

The anti-wear additives useful are the oil-soluble zinc dihydrocarbyldithiophosphates having a total of at least 5 carbon atoms, the alkyl group being preferably C$_5$–C$_8$, typically used in amounts of about 1–6% by weight.

Suitable conventional viscosity index improvers, or viscosity modifiers, are the olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrollidone or dimethylaminoalkyl methacrylates, post-grafted polymers of ethylene-propylene with an active monomer such as maleic anhydride which may be further reacted with alcohol or an alkylene polyamine, styrene-maleic anhydride polymers post-reacted with alcohols and amines and the like. These are used as required to provide the viscosity range desired in the finished oil, in accordance with known formulating techniques.

Examples of suitable oxidation inhibitors are hindered phenols, such as 2,6-di-t-butyl-para-cresol, amines, sulfurized phenols and alkyl phenothiazones; usually a lubricating oil will contain about 0.01 to 3 weight percent of oxidation inhibitor depending on its effectiveness.

Rust inhibitors are employed in very small proportions such as about 0.1 to 1 weight percent with suitable rust inhibitors being exemplified by $C_9$–$C_{30}$ aliphatic succinic acids or anhydrides such as dodecenyl succinic anhydride.

Antifoam agents are typically the polysiloxane silicone polymers present in amounts of about 0.01 to 1 weight percent.

While a wide variety of lubricating oil base stocks may be used in preparing the composition of this invention, most typically mineral oils having a viscosity of about 2–40 centistokes (ASTM-D-445) at 99° C. are employed.

The invention is further illustrated by the following examples which are not to be considered as limitative of its scope.

EXAMPLE I—VIB RESULTS

A lactone oxazoline and a bis-oxazoline dispersant were prepared and complexed with either copper thiocyanate or copper acetate by reacting the mixture at about 55° C. for 2 hours in mineral oil. The products were evaluated in the Varnish Inhibition Test and compared with the same oxazoline and lactone oxazoline dispersants prior to their complexing with copper.

The lactone oxazoline dispersant was prepared by first lactonizing a polyisobutenyl succinic anhydride of molecular weight of 1300 and a Saponification No. of 49 with $H_2SO_4$ for three hours and thereafter reacting with an equimolar quantity of THAM at 180° C. for about four hours; the procedure being fully disclosed in U.S. Pat. No. 4,062,786.

The bis-oxazoline was prepared from a polyisobutenyl succinic anhydride of molecular weight 1300 and saponification No. 103 by heating about 1 mole of the polyisobutenyl succinic anhydride with about two moles of THAM as a 40% aqueous solution and 3.4 grams of zinc acetate over a period of two hours to form the bis-oxazoline dispersant. The results are tabulated below followed by a description of the Varnish Inhibition test.

TABLE I

| VIB TEST RESULTS | | | |
|---|---|---|---|
| Dispersant | % N | % Cu | VIB Rating |
| (A) Lactone | 0.52 | None | 7 |
| (B) CuSCN Complex of (A) | 0.52 | 2.27 | 5 |
| (C) Bis-oxazoline | 0.88 | None | 6½ |
| (D) Cu SCN Complex of (C) | 0.88 | 1.55 | 4 |
| (E) Cu SCN Complex of (C) | 0.88 | 1.64 | 4½ |
| (F) Cu Acetate Complex of (C) | 0.88 | 1.20 | 5 |

In the VIB Test, a test sample consisting of ten grams of lubricating oil containing the additive being evaluated is used. The test oil is a commercial lubricating oil obtained from a taxi after two thousand miles of driving with said lubricating oil. Each sample is heat soaked overnight at about 140° C. and thereafter centrifuged to remove the sludge. The supernatant fluid of each sample is subjected to heat cycling from about 150° C. to room temperature over a period of 3.5 hours at a frequency of about two cycles pr minute. During the heating phase, a gas containing a mixture of 0.7 volume percent $SO_2$, 1.4 volume percent NO, and the balance air, was bubbled through the test samples, and during the cooling phase, water vapor was bubbled through the test samples. At the end of the test period, which testing cycle can be repeated as necessary to determine the inhibiting effect of any additive, the wall surfaces of the test flasks in which the samples were contained are visually evaluated as to the extent of varnish inhibition. The amount of varnish imposed on the walls is rated at values of from one to seven with the higher number being the greater amount of varnish. It has been found that this test correlates with the varnish results obtained as a consequence of carrying out engine tests.

EXAMPLE II—OXIDATION RESULTS

The anti-oxidant benefits of the dispersants of this invention were evaluated in the LMOT (Laboratory Multiple Oxidation Test) in which 50 ml of test fluid with 2.0 g of iron filings and 0.5 g of a 1% solution of copper naphthenate is heated to 150° C. and 25 ml air per minutes is passed through the sample. Daily samples are taken and the number of days for visible sludge to appear on blotter paper is recorded. For mineral oils containing 2% of dispersant (A) of Example I, the LMOT value was less than 2 days but the same oil having 2% of dispersant (B) showed an improvement to 4 days. In base oils containing 0.3 wt% of a conventional $P_2S_5$-pinene antioxidant, dispersant (A) at 2% gave a value of 7 days but a sample of the same oil with dispersant (B) at 2% showed an improvement to 9 days.

What is claimed is:

1. A lubricating oil composition comprising a major amount of lubricating oil and a minor but varnish inhibiting and oxidation inhibiting amount of an oil soluble copper complex of an oil soluble hydrocarbon substituted mono- or bis-oxazoline or hydrocarbon substituted lactone oxazoline dispersant, the copper being present in said complex in an amount of about 0.2 to 2.0 wt% of said mono-oxazoline, bis-oxazoline or lactone oxazoline.

2. The composition of claim 1 wherein said mono- or bis-oxazoline is the reaction product of a polyisobutenyl succinic anhydride with a $C_4$–$C_8$ amino alcohol of the formula $NH_2$—$C(X)_2$—$CH_2OH$ where X is alkyl or hydroxyalkyl, at least one X being hydroxyalkyl of the formula —$(CH_2)_mOH$, m being 1–3.

3. The composition of claim 2 wherein the amino-alcohol is tris-(hydroxymethyl) aminomethane.

4. The composition of claim 1 wherein the dispersant is a lactone oxazoline formed by the reaction of a lactonized polyisobutenyl succinic anhydride with at least equimolar proportions of a $C_4$–$C_8$ amino-alcohol of the formula $NH_2$—$C(X)_2$—$CH_2OH$ wherein X is alkyl or hydroxyalkyl, at least one X being hydroxyalkyl of the formula —$(CH_2)_mOH$, m being 1–3.

5. The composition of claim 4 wherein the amino-alcohol is tris-(hydroxymethyl)aminomethane.

6. The composition of claim 1 wherein the hydrocarbon substituent is polyisobutenyl of Mn 900 to 2,000.

7. A process for preparing a copper complex of an oil soluble hydrocarbon substituted mono-oxazoline, bis-oxazoline, lactone or oxazoline lubricating oil dispersant comprising reacting said dispersant with a complex-forming copper compound selected from the group consisting of copper carboxylates of $C_1$–$C_5$ carboxylic, acids, copper oxides and copper thiocyanates at temperatures of 50° C.–200° C. for about 2–10 hours in an inert hydrocarbon solvent.

* * * * *